United States Patent [19]

Shishido

[11] Patent Number: 4,700,694

[45] Date of Patent: Oct. 20, 1987

[54] ENDOSCOPE MEANS AND OVUM PICKER EMPLOYED BY INSERTING THROUGH ENDOSCOPE MEANS

[75] Inventor: Yoshio Shishido, Sagamihara, Japan

[73] Assignee: Olympus Optical Co., Ltd., Tokyo, Japan

[21] Appl. No.: 703,364

[22] Filed: Feb. 20, 1985

[30] Foreign Application Priority Data

Feb. 20, 1984 [JP] Japan ............................. 59-30075
Feb. 24, 1984 [JP] Japan ............................. 59-35022

[51] Int. Cl.⁴ ............................................. A61B 1/06
[52] U.S. Cl. ......................................... 128/6; 128/4; 604/158
[58] Field of Search ..................... 128/4, 8, 6, 3, 5, 7; 604/56, 158, 164, 264, 167

[56] References Cited

U.S. PATENT DOCUMENTS

| | | | |
|---|---|---|---|
| 1,880,551 | 10/1932 | Wappler | 128/7 |
| 4,000,739 | 1/1977 | Stevens | 604/167 X |
| 4,252,122 | 2/1981 | Halvorsen | 604/164 |
| 4,538,594 | 9/1985 | Boebel et al. | 128/6 |
| 4,607,619 | 8/1986 | Seike et al. | 128/4 |
| 4,653,475 | 3/1987 | Seike et al. | 128/4 |

FOREIGN PATENT DOCUMENTS

7615524 10/1976 Fed. Rep. of Germany .
8104329  6/1981 Fed. Rep. of Germany .
8322900 11/1983 Fed. Rep. of Germany .

Primary Examiner—William H. Grieb
Attorney, Agent, or Firm—Armstrong, Nikaido, Marmelstein & Kubovcik

[57] ABSTRACT

This invention relates to means for picking up the ovum from the ovarian follicle of mother's body for external fertilization and, more especially, to endoscope means and tool for picking up the ovum wherein the ovum is picked up under visual observation by means of an endoscope and the tool for picking up the ovum is employed by inserting it through the channel of the endoscope so that the abdominal wall of the mother's body is only provided with a hole for inserting the endoscope. The tool for picking up the ovum comprises a fine tube having a small hole at the tip thereof inserted slidably through a sheath tube and having cutting edge at the tip thereof into the ovarian follicle and by aspirating an aspirator needle or fine tube protruded from the small hole.

3 Claims, 18 Drawing Figures

ENDOSCOPE MEANS AND OVUM PICKER EMPLOYED BY INSERTING THROUGH ENDOSCOPE MEANS

BACKGROUND OF THE INVENTION

1. Field of the Invention

This invention relates to endoscope means incorporating a channel and ovum picker inserted through the channel and for picking up ovum from the ovarian follicle without injuring the follicle and for accomplishing this under the visual observation through an endoscope means.

2. Description of the Prior Art

Since the first success in the birth of externally fertilized babies by Steptoe in the United Kingdom in 1978, interests in external fertilization has increased all over the world including Japan. Clinical applications have been tried in various facilities. There have been reported about 400 cases of birth of babies externally fertilized.

In order to effect the external fertilization, it is necessary to pick up the ovum from the mother. As reported by Mr. Suzuki et al in the Medical Department of Tohoku University on Journal of Japanese Sterlization Society, No. 4, Vol. 28, 1983, the ovum has been picked up by sucking it through a suction needle inserted through a hole formed through abdominal skin under the observation through an abdominal endoscope inserted through as second hole pierced through the abdominal skin.

Conventional aspirator needle, as employed for sucking up the ovum, has the form a hollow needle for a syringe, having a inner diameter of about 1.0 mm for picking up the ovum, an outer diameter of about 2.0 mm and a length of about 200 to 250 mm. Such needle has a sharp edge at the top thereof for piercing through the ovarian follicle grown at the surface of ovary. The precious ovum, developed during long menstruation, has frequently been injured by the sharp edge of needle during piercing.

If damage caused by the piercing needle is not found and fertilization succeeds, a defective baby will be born. Hence, care must be exercised for the picking-up of ovum by the piercing needle, external fertilization and implanation or pregnancy.

For picking-up of ovum, the needle should be pierced through the ovarian follicle. The sharp tip edge of the aspirator needle in such conventional practice should be pierced deeply, after the piercing for aspirating and can result in the damage on the ovum in the ovarian follicle. Particularly, when such is procedure is to be applied to human beings, the picking-up of ovum is very dangerous.

Moreover, when a fine hole or opening is provided for aspirating and picking-up ovum and the tip of aspirator needle is protruded, the ovarian follicle is displaced making the formation of a suitable opening, such as fine hole, difficult. Excessively piercing with the sharp needle edge can damage the inner ovum. Still further, the conventional aspirator needle has the additional disadvantage in that the ovarian follicle is displaced easily and can be pierced at an undesired site.

In addition, because the conventional aspirator needle requires one piercing hole and the abdominal endoscope requires a second hole for picking up the ovum through the abdominal wall, the needle method is not favorable for patient or animal.

A picking-up tool of ovum for external fertilization is described in West Germany Utility Model No. 7,615,524. An endoscope incorporating a channel is shown, for example, in U.S. Pat. No. 4,252,122 and West Germany Utility Model No. 68,104,329.

SUMMARY OF THE INVENTION

It is a principle object of this invention to provide endoscope means wherein the inlet mouth or channel through the endoscope is partitioned into a plurality of compartments for inserting a plurality of tools, such as a tool for picking up ovum and clamping forceps concurrently through the channel. The tool for picking up the ovum is pierced through the ovarian follicle. The pick up tool and clamping forceps are manipulated for picking up the ovum safely and accurately.

It is another object of this invention to provide endoscope means wherein the endoscope and tool for picking up the ovum can be inserted integrally through the abdominal wall by providing a single piercing hole therethrough. The ovum within the ovarian follicle can be picked up under the visual observation through the endoscope means, thereby mitigating the pain of the patient and improving the operability of surgeons.

It is a further object of this invention to provide a tool for picking up the ovum wherein the aspirator needle or capillary tube is designed to be movable through the sheath tube for aspirating and picking up the ovum from the ovarian follicle and to be fixative with the sheath tube by the manipulating the needle at the handle side to pick up the ovum safely and efficiently without injuring the ovum, etc.

It is still further object of this invention to provided a tool for picking up the ovum which can be operated by a single operator or a small number of operators.

It is still further object of this invention to provide a tool for picking up the ovum by using a sharp edge at the tip of sheath only when a fine opening is pierced through the ovarian follicle and by aspirating and picking up the ovum through a capillary tube or aspirator needle having rounded tip without injuring the ovum.

It is still further object of this invention to provide a tool for picking up the ovum which is operable easily by functioning the aspirator needle as the guide, as compared with conventional tool, wherein the pick-up operation is carried out exclusively by the aspirator needle.

It is still more object of this invention to provide a tool for picking up the ovum effectively by draining physiological soldium chloride solution, a gas or, the like, into the ovarian follicle for preventing the contraction thereof.

In brief, this invention is designed so as to provide a plurality of inserting mouths by partitioning the mouth of channel inserted through the endoscope means for inserting a tools for picking up the ovum from one mouth through the channel and for inserting, concurrently, auxiliary means of the picking-up operation from another mouth through said channel.

The tool for picking up the ovum is incorporated with a capillary tube having a tip of rounded converged form, such as spherical point, and provided with a fine hole at the tip, aspirating and picking-up means comprising an aspirating needle or capillary tube capable of picking up the ovum by aspirating it through a fine hole, provided at the tip of means protruded from the fine hole at the rounded tip, and a sheath tube incorporating slidably in the axial direction of said capillary tube and provided with a sharp edge at the tip thereof.

Moreover, the tool for picking up the ovum is provided with means for fixedly clamping the aspirating and picking-up means so as not be movable in the axial direction.

The above-mentioned and other purposes and advantages achieved by this invention will be obvious from the following description.

BRIEF DESCRIPTION OF THE DRAWINGS

FIGS. 1 to 13 relate to a first embodiment of this invention.

FIGS. 14 to 18 relate to a second embodiment of this invention.

DETAILED DESCRIPTION

FIGS. 1 to 13 illustrate a first embodiment of this invention. As seen from FIG. 1, abdominal endoscope 1 comprises a rigid and elongated insert member 2, body member 3 having a large diameter or large width and connected the leading end thereof with the trailing end of said insert member 2, first channel 4 connected in alignment with insert member 2 at the trailing end of body member 3, second channel 5 branched obliquely backwards and downwards from first channel 4 and eyepiece member 6 connected obliquely backwards and upwards from the side of body member 3.

Figures 1, 2, 3:
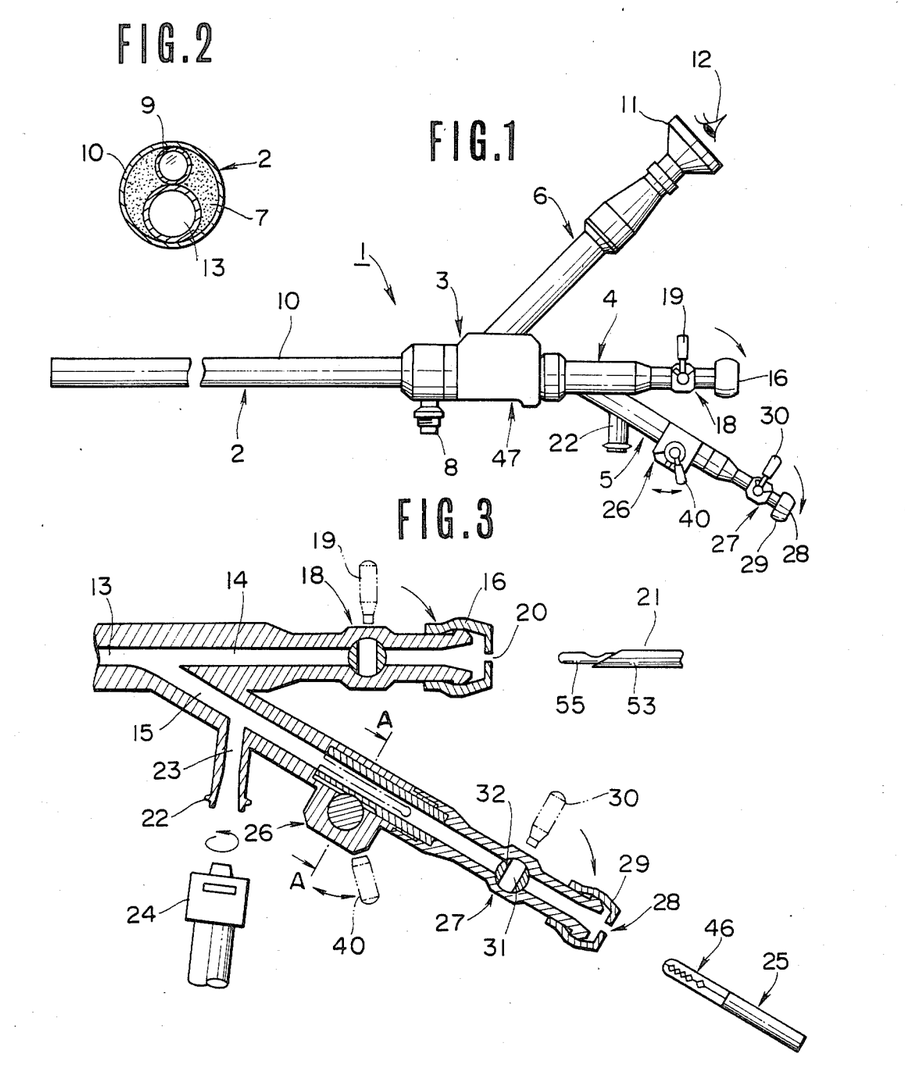
FIG. 1 shows a abdominal endoscope, or laparoscope, by inserting the first embodiment.
FIG. 2 is an enlarged front view of the abdominal endoscope of FIG. 1.
FIG. 3 is enlarged sectional view of the handle of the abdominal endoscope of FIG. 1.

Through insert member 2 of the abdominal endoscope, there is inserted light guide 7 comprising bundle of very fine optical fibers for transmitting illuminating light. Light guide 7 is bent at the body member 3 and the trailing end thereof is fixed to light guide mouthpiece 8. Illuminating light is transmitted from a light source (not shown) through a light cable (not shown) connected to mouthpiece 8 and through light guide 7 and emitted through the leading end of light guide to a forward portion to be irradiation (i.e. an organ) as shown in FIG. 2. In addition, pipe or tube 9 for receiving the observation optical system is inserted through sheath tube 10 eccentrically upwards of member 2. The front end of pipe 9 is sealed with cover glass and pipe 9 receives an objective lens system, relay lens system or image guide for transmitting the focused image by said objective lens system to transmit the image to eyepiece member branched from body member 3 through an eyepiece lens system (not shown) to eyepiece 11 for observing the magnified image with eye 12.

A hollow pipe is inserted through the insert member 2 eccentrically downwards in the vicinity of pipe 9. Through the hollow portion, there is defined so-called forceps channel 13 through which can insert operating tool and like. As shown in enlarged FIG. 3, forceps channel 13 is connected, respectively, with hollow passages 14, 15 within first channel 4 and second channel 5 each branched at the trailing portion of body member 3.

Passage 14, within first channel 4, is connected with channel 13 in alignment therewith and attached with rubber cap 16, at the trailing end, and cock 18 at the midway for opening passage 14 by turning lever 19 to the direction of arrow or for closing the passage by turning the lever to the opposite direction.

Rubber cap 16 has hole 20 having a size smaller than the outer diameter of ovum pick up tool 21 so as to maintain air tightness when tool 21 is inserted forwards through hole 20 and cock 18 in FIG. 3 is opened.

Channel 5 is branched from channel 4 so as to be extended obliquely downwards and is provided with cock mouthpiece 22 protruded downwards slightly downstream from the branched position. Passage 15 is connected with passage 23 within cock mouthpiece 22 so as to feed a veress gas from a veress cannula (not shown) by connecting cock connector 24 with said cock mouthpiece 22.

Clamping and fixing means 26 is provided within channel 5 at a downstream position from the position provided with cock mouthpiece 22 so as to fix firmly clamping forceps 25 inserted through passage 15 within channel 5. Cock 27 is provided at a further downstream position from said clamping means 26. Inserting mouth position, at a downstream position from said cock 27, is capped with rubber cap 29 provided small central hole 28.

Cock 27 is designed to close or open passage 15 by pivoting plug 32 provided with open passage 31 by pivoting rectangularly lever 30. (Cock 18 provided within first channel 4 has similar structure.)

Figure 4:
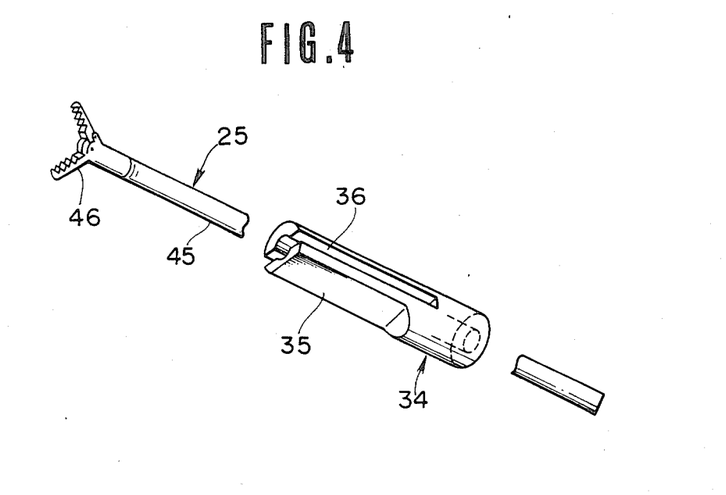
FIG. 4 shows a pressure welded member forming the clamping and fixing means of the abdominal endoscope.
Figure 5:
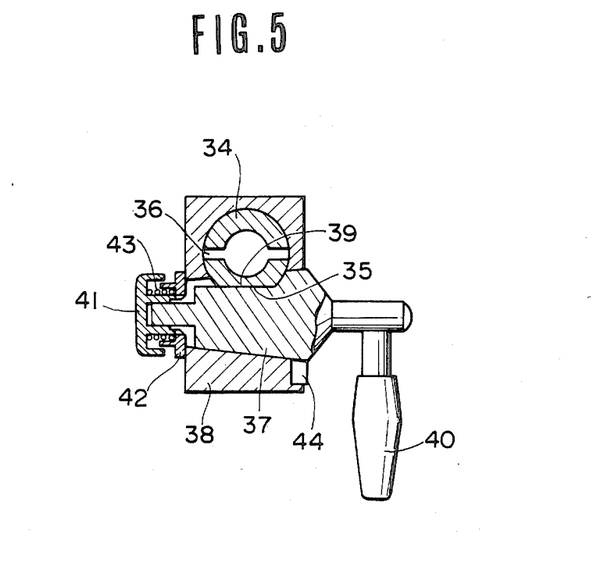
FIG. 5 is a sectional view of clamping and fixing means taken along line A—A in FIG. 3.

Clamping and fixing means 26 have a structure as illustrated by FIGS. 4 and 5.

Means 26 comprises contact member 34 fitted in channel 5 for define a portion of passage 15 and compression member for clamping forceps 25 inserted through the hollow portion of the pressure contact member 34 by pressing flat member formed by notching the outer periphery of contact member 34 lengthwise to an appropriate length, or the like, and reducing the width of splitted groove 36 formed by notching lengthwise so the the splitted groove is parallel to flat member 35, or the like. Compression member 37 is formed, for example, by a semi-hard rubber or plastic material and received through the tapered through hole formed through main body 38 of clamping and fixing means 26, as shown in FIG. 5. The outer tapered periphery of compression member 37 is contacted firmly with the tapered through hole and notched, or the like, to form a flat recess 39 to be fitted with flat member 35 of contact member 34, as shown in FIG. 5. Under such a condition, contact member 34 has predetermined normal inner diameter so as to receiving inserted clamping forceps 25. When lever 40, at one end of compression member 37, is pivoted, flat member 35 is turned and contact member 34 is pressed against the tapered portion to reduce the width of splitted groove 36 and clamp the shaft of clamping forceps inserted through the inner portion over a wide contact area to firmly fix the forceps so as not to be slidable axially.

The end of compression member 37 opposed to the end attached with the lever 40 is lathed stepwise to a small diameter and closed by threading cap nut 41. Cap 41 nut is biased to the direction opposed to compression member 37 by spring 43 between said nut and washer member 42 so as to keep air and water tightness by means of a small amount of grease between the outer tapered ground periphery of compression member 37 and the inner tapered ground periphery of the through hole. Moreover, pin 44 is provided protrudedly from the outerperiphery of compression member 37 and acts as a stopper for controlling the range of pivotal angle of lever 40.

A wire (not shown) is inserted through elongated, flexible and hollow shaft 45 so that alligator mouth 46, provided pivotably at the tip of shaft 45 as shown in FIG. 4 is opened, for example, by relaxing the wire and manipulate at the handle (not shown) to close the clamp on the desired objective organ by retracting the wire.

Holding member 47, for holding body member 3, is provided by flattening the backward portion from light guide mouthpiece 8, or the like.

Tool for picking up ovum 21 according to the first embodiment is inserted freely through first channel 4 of abdominal endoscope 1 and comprises picking-up needle 59 and hollow aspirator needle 52 capable to be inserted through the inner hollow passage of said picking-up needle 59 and acting as means for aspirating and picking up ovum.

Picking-up needle 59 comprises elongated sheath tube 53 to be insertable from the inserting mouth at the trailing end of first channel 4 through forceps channel 13 in the abdominal endoscope, operative member 54 formed by securing firmly a tubular or cylindrical member having a larger diameter with the trailing end of said sheath tube 53 and provided with a knurled pattern for clamping and handling the sheath tube easily and fine hollow tube 55 attached slidably to the axial direction (longwise direction) within the sheath tube.

Figure 6:
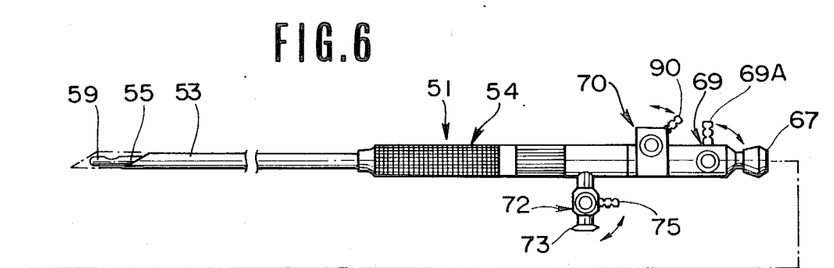
FIG. 6 shows a tool for picking up ovum of the first embodiment.
Figure 7:
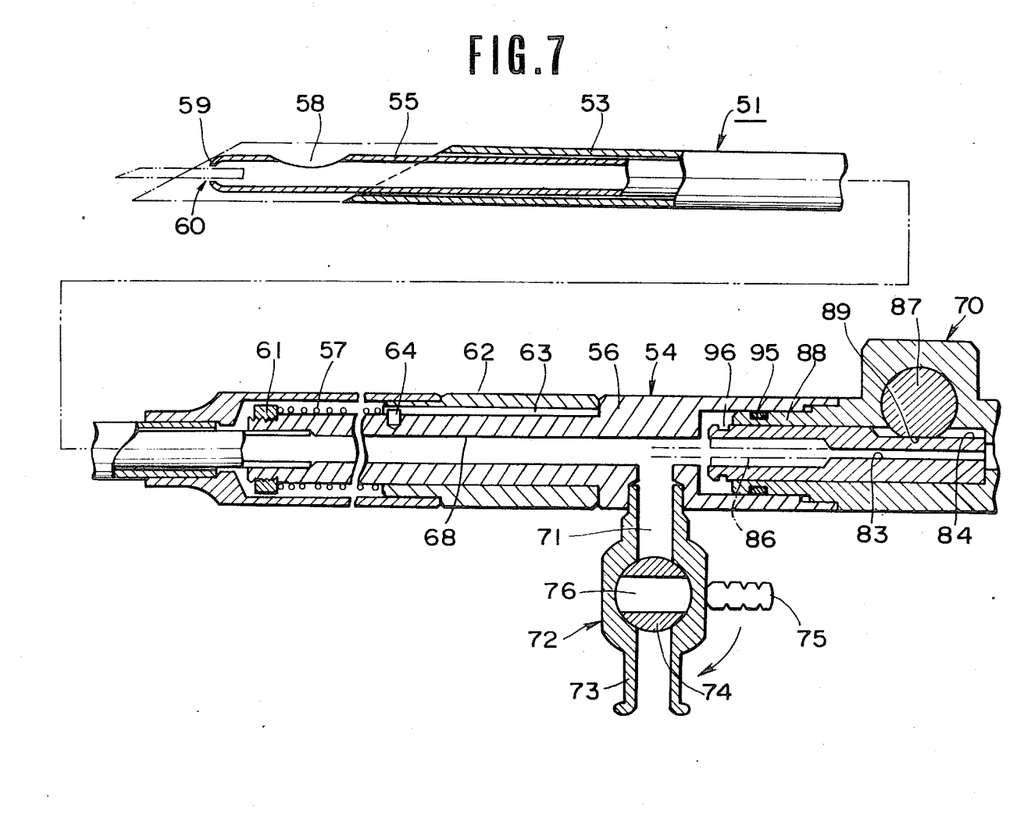
FIG. 7 shows an enlarged view of aspirator needle of FIG. 6.

As shown in FIG. 7, fine hollow member 55, within sheath tube 53, is secured at the trailing end thereof with the leading end of inner periphery of thick-walled and substantially tubular body of handle member 56, FIG. 7. Fine hollow member 55 is biased axially forwards together with the handle member 56 by means of spring 57 fitted through the clearance defined between the outer periphery of front half of handle member 56 and the surrounding inner periphery of cylindrical member of operative member 54 as shown by FIG. 7. In short, as shown in FIG. 6 and FIG. 7, the tip of fine hollow member 55 is protruded to an appropriate length from the tip formed into sharp edge by cutting the hollow member obliquely under the normal condition. The tip of said fine hollow member 55 is provided with a hole, i.e. side hole 58 so as to irrigate a gas or sodium chloride solution therethrough. Additionally, converged tip 59a having spherical or round form is formed at the front of said side hole 58. Fine hole 60 is pierced through the converged tip so that aspirator needle 52 is inserted along the central axis of fine hollow member 66 is protruded through small hole 60.

Spring 57 for biasing fine hollow member 55 to be protruded through small hole 60 is controlled by abutting the leading end thereof with the leading end of handle member, for example with nut 61 threaded into handle member 56, and the trailing end of the spring is controlled by abutting the trailing end against the leading end of cylindrical sliding member 62 connected at the trailing end of cylindrical member comprising operative member 54 and telescoped around the outer periphery of handle member 56. Sliding member 62 is provided with elongated axial groove 63, for example, on the upper side of inner periphery fitted through handle member 56 for receiving guide pin 64 at a position so that when the tip of fine hollow member 55 is displaced backwards, by pressing, hollow member 56 is contracted longitudinally and guide pin 64 is also displaced backwards through elongated groove 63. When guide pin 64 is abutted against the furthermost trailing end of elongaged groove 63, tip 59 of fine hollow member 55 is positioned within the obliquely cut tip of sheath tube 53. It should be noted, in FIG. 6 and FIG. 7, that sheath tube 53 cannot be displaced from the position as shown in the solid line to the position as shown by one dot chain line but, when fine hollow member 55 is retracted backwards, the tip of fine hollow member 55 is retracted within sheath tube 53 as shown by dot chain line.

Moreover, fine hollow member 55 is attached normally so that side hole 58 is positioned at the position protruded from the tip of sheath tube 53. Such position may be precisely adjusted, for example, by the position for fixing nut 61, or alternatively, for example, by protruding another pin forwards from handle member 56 to the position apart from the leading end of sliding member 62.

Spring 57, for biasing fine hollow member 55 so as to protrude tip 59 of fine hollow member 55, is designed so that the spring is contracted together with the elastic member comprising handle member 56 by a weak force for abutting tip 59 of fine hollow member 55 against the ovarian follicle and pressing it further. Under such a condition, the sharp edge of sheath tube 53 is protruded for piercing the edge into the follicular membrane.

Figure 8:
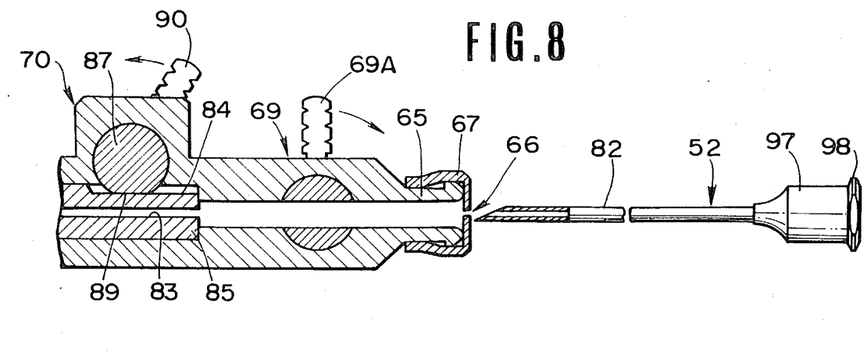
FIG. 8 shows a peripheral view of the trailing end of the aspirator needle shown in FIG. 6.

The latter half portion adjacent to the portion attached with sliding member 62 of handle member 56 has thick stepped wall and the trailing end of handle member is internally lathed so as to form cock mouthpiece 65 as shown in FIG. 8. cock mouthpiece 65 is covered with rubber cap 67 provided with central small hole 66 so as to insert aspirator needle 52 forwards through small hole 66.

There is provided cock 65 at the thick-walled portion of handle member 56 at a slightly forward position from cock mouthpiece 65 so that when aspirator needle 52 is not inserted through hollow passage 68, the opened passage 68, through cock mouthpiece 65, is closed by pivoting lever 69A.

In addition, there are provided holding and fixing means 70 for securing aspirator needle 52 inserted through the hollow passage 68 in handle member 56 at a slightly forward position of cock 69 and cock 72 provided with through hole 71 connecting to hollow passage 68 of handle member 56, for example, so as to protrude downwards at a forward position of the holding and fixing means. Cock 72 has a structure as illustrated, for example, by FIGS. 7, 9 and 10.

Figure 9:
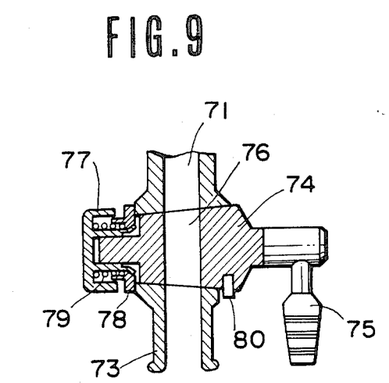
FIGS. 9 and 10 show the structure of the cock for the aspirator needle.
Figure 10:
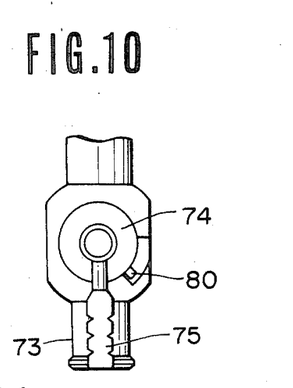
Figure 11:
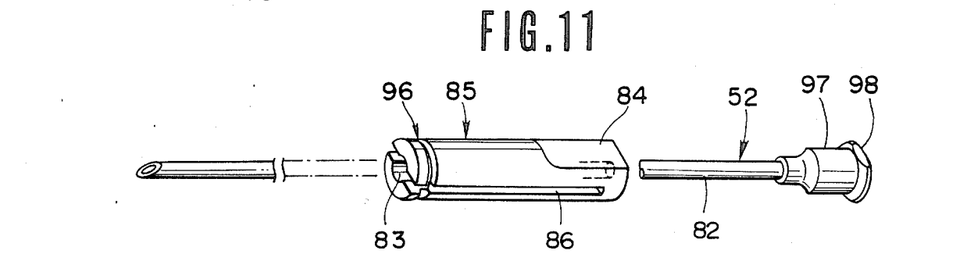
FIG. 11 show a pressure welded member formed on the aspirator needle for the clamping and fixing means.

Through hole or passage 71, within cock 72, connects cock mouthpiece 73 with hollow passage 68 of handle member 56. Cock 72 is provided with a through hole having a diameter larger than through hole 71 and the hole is attached with plug 74. The through hole has a tapered passage therein and a larger diameter at one end. Ground plug 74 is attached so as to maintain the tightness by the ground surfaces. Plug 74 is tapered to the trailing end and attached with lever 75 protrudedly and rectangularly at the trailing end so that plug 74 is pivoted by the pivoting rectagularly lever 75 for connecting hole 76 with through hole 71, as shown in FIGS. 9 and 10, or for blocking the through hole 71 as shown in FIG. 7. The end of plug 74 protruded to the direction opposite to the end provided with lever 75 is stepped to a smaller diameter and connected with nut 77. Nut 77 defines a recess around the outer periphery of stepped end of plug 74 for receiving spring 79 within the recess and between the confronted washer member 78 for pressing nut 77 to the direction opposed to plug 74 by the action of spring 79 so that the plug is contacted firmly with the ground portion of cock 72 so as to maintain gas tightness and liquid tightness.

Pin 80, provided protrudedly to plug 74, acts as a stopper for controlling the range of pivotal angle of lever 75.

Cock 69 has a similar structure.

Holding and fixing means 70 holds and fixes aspirator needle 52, inserted forwards through rubber cap 67 for picking-up needle 51, so as not to slide it axially and has a structure as shown in FIGS. 7, 8, 11 and 12.

Clamping means 70 comprise contact member 85 having flat member 84 formed, for example, by notching the outer periphery of cylindreical or tubular member defining inserting hole 83 for receiving hollow member 82 of aspirator needle 52 longitudinally to an appropriate length, compression member 87 for reducig the effective inner diameter of inserting hole 83 by reducing the width of splitted groove 86 formed longitudinally along said contact member 85 by pressing flat member 84 of contact member 85 and main body 88 of holding and fixing means 70 comprising a housing for receiving contact member 85 and compression member 87.

Figure 12:
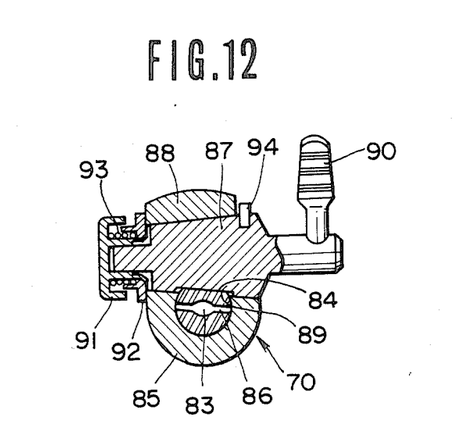
FIG. 12 shows a sectional view of clamping and fixing means formed for the aspirator needle.

Compression member 87 is formed into a fulcrum or cone ground fitted through the inner wall of tapered through hole formed through mainbody 88 of the holding and fixing means. Recess 89 is formed on the outer conical periphery surface in firm contact with the inner wall surface of the through hole, for example, by notching. The inner bottom surface of recess 89 is flattened and fitted with flat member 84 of contact member 85 as shown in FIG. 7 and 12. Under the fitted codition, the inner diameter of through hole 83 of contact member 85 slidably receives hollow member 82 of aspirator needle 52 and means 70 can hold and fix aspirator needle 52 by pivoting lever 90 provided protrudedly at one end of contact member 85 to press flat member 84 of contact member 85 which has been closely contacted with the flat member of recess or notch 89 by the tapered corner portion of recess 89, thereby reducing the width of splittered groove 85 of contact member 85 and reducing the effective inner diameter of through hole 83. Hollow member 82 of aspirator needle 52 is prevented from the deformation or collapse thereof by pressing and fixing aspirator needle 52 by means of contact member 85 provided with splitted groove 86 in lieu of direct compression and fixation, thereby increasing contact area with aspirator needle 52. Such compression and fixation can be relieved easily by pivoting lever 90.

The end of compression member 87, opposed to the end attached with lever 90, is stepped to a small diameter as shown in FIG. 12 and threaded with cap nut 91. Nut 91 closely contacts the ground portions of outer tapered periphery of compression member 87 and inner wall surface of tapered through hole to maintain gas tightness and hydraulic tightness by biasing nut 91 to the direction opposed to compression member 87 by means of spring 93 between nut 91 and confronted washer member 92. Pin provided protrudedly from the outer periphery of compression member 87 is a stopper for controlling the range of pivotting angle movement of lever 90.

Main body 88 of the holding and fixing means receives contact member 85. As shown in FIG. 7, the outer periphery of main body 88 is provided with a recess around the trailing end for fitting O-ring 95 therearound and for inserting firmly through the lathed inner periphery of handle member 56 at the trailing end thereof to maintain the gas tightness and hydaulic tightness. In addition, groove 96 is formed around the outer periphery of contact member 85 at the vicinity of leading end thereof for pinching easily with fingers in the diassembling of contact member 85 from compression member 87. Moreover, inserting hole 83 is lathed around the leading portion from flat member 84 f contact member 85 so as not to contact the inner periphery of hole 83 excessively with the outer-periphery of hollow member 82 of aspirator needle 52 and to minimize the friction of sliding hollow member 82 when inserted aspirator needle is not pressed to be fixed.

Aspirator needle 52, inserted through said picking-up needle 51, comprises elongated hollow member 82 and handle member 97 having a larger diameter at the trailing end. There is formed cock mouthpiece 98 at the trailing end of handle member 97 so as to be connected with an aspirator such as syringe, or the like, by means of a tube, or the like.

Figure 13:
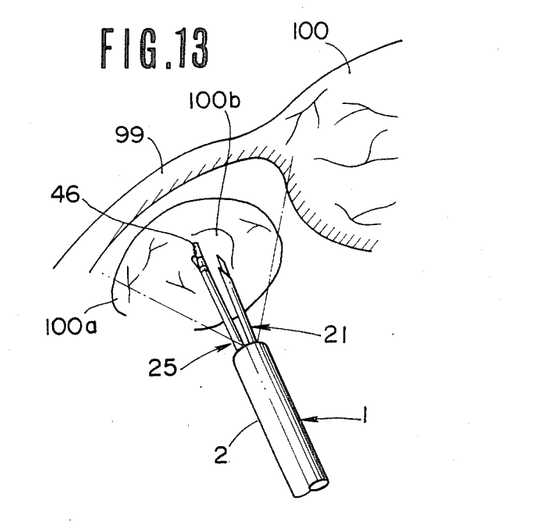
FIG. 13 shows the picking up of the ovum by means of the first embodiment.

There will be now set forth how to employ the abdominal endoscope according to the first embodiment for picking up the ovum by way of FIG. 13.

When an alveoclar ovarian follicle is possibly grown on the surface of ovary, the abdominal wall is provided with a guide hole by pierceing a trocar. Insert member 2 of abdominal endoscope 1 is inserted through the guide hole and veress gas is infused through cock mouthpiece 22 formed at the vicinity of branch of second channel 5 for facilitating the insertion of abdominal endoscope 1 and the observation and subsequent operation for picking up the ovum. The fallopian tube 99 connected to uterus 100 and ovary 100a are observed by means of optical system for the observation at the tip of insert member 2 by inserting insert member 2 of abdominal endoscope 1. When the presence of alveoclar ovarian follicle 100b is conformed on the surface of ovary, clamping forceps 25 is inserted forwards from the trailing end of second channel 5 of abdominal endoscope 1 through passage 15 in said channel 5 and picking-up needle 51 is inserted forwards from the trailing end of first channel 4 through passage 14 is channel 4.

Under the observation by abdominal endoscope 1 supported by one hand of operator, the vicinity of grown ovarian follicle 102 is clamped by means of alligator mouth 46 at the tip of clamping forceps 25 by operating the handle side of clamping forceps 25 protruded forwards through forceps channel 13 of abdominal endoscope 1 and locked the clampling forceps 25 under the clamping condition by pivoting lever 40 for clamping and fixing means 26. Compression member 37 presses flat member 35 of contact member 34, provided with splitted groove 36, by the pivotal operation of lever 40 to reduce the effective inner diameter and to hold and fix clamping forceps 25 inserted through forceps channel 13 firmly and on-slidably longitundinally. Accordingly, the operator can detach his hand from secured clamping forceps 25 and can cat to protrude picking-up needle 51 through the leading end of forceps channel 13 of the first embodiment.

In such a case, aspirating needle 52 is provisonally inserted from the trailing end of picking-up needle 51 therethrough so that the tip of the latter needle is retracted slightly from the tip of sheath tube 53 and hollow member 82 for aspirator needle 52 is fixed by pivoting lever 90 for holding and fixing means 70.

Compression member 87 presses flat member 84 of contact member 85 by pivoting lever 90 to reduce the effective inner diameter of inserting hole 83 for contact member 85 and to press hollow member 82 fo aspirator needle 52 for fixing it firmly and non-slidably longitudinally.

Under such a conditon that the aspirator needel 52 is fixed, the tip of picking-up needle 51 is abutted against alveoclar ovarian follicle 100b to be picked up under the observation by means of abdominal endoscope 1 and pressed gently forwards. Then the tip of fine hollow member 55 is retracted by the pressing to protrude the tip sharp edge of sheath tube 53, thereby forming a small opening. When the opening is enlarged to a size cabable to insert the converged tip of the hollow member 55, the piercing of sharp edge of sheath tube 53 is stopped to relieve the pressure of tip 59 of fine hollow member 55 agains the membrane of ovarian follicle so that tip 59 of hollow member 55 is protruded automatically through the opening to be inserted into ovarian follicle 100b. In such a case, the vicinity of ovarian follicle 100b is clamped and fixed by alligator mouth 46 at the tip of clamping forceps 25 so that ovarian follicle 100b can be assured to be immobile in position when the protruded tip of picking-up needle 51 presses ovarian follicle 100b to be pierced safely and correctly to the desired portion to form an opening for picking up the ovum. In addition, tip 59 of fine hollow member 55, inserted through the opening, is rounded so as to be inserted without danger for injuring the ovum even when tip 59 is inserted into a substantial depth in ovarian follicle 100b. When tip 59 of fine hollow member 55 is to be inserted, biological sodium chloride solution is infused through cock mouthpiece 73 formed within handle member 56 of picking-up needle 51 to maintain ovarian follicle 100b under non-contracted normal condition or swollen condition, aspirator needle 52 inserted through picking-up needle 51 and fixed so that the tip of the latter neeedl is retracted to some extent from the tip of sheath tube 53 is relieved from the fixation by the pivotal motion of lever 90 and displaced forwards. When the tip of aspirator needle 52 is protruded through small hole 60 of fine hollow member 55 to an appropriate depth into ovarian follicle 100b, the ovum is aspirated and received together with the saline water within hollow member 82 by displacing backwards the piston of aspirator of syringe type connected via a tube with cock mouthpiece 98 formed at handle member 97 for aspirator needle 52. The aspirator needle is withdrawn from picking-up needle and lever 69A of cock 69.

As mentioned hereinbefore, the ovum can be picked up into aspirator tube by a simple manner.

According to the first embodiment, holding and fixing means 70 are provided for aspirator needel 52 so that when the ovum is picked up by inserting picking-up needle 51 through channel 13 of abdominal endoscope 1, picking-up needle 51 is inserted through aspirator needle 52 and can be fixed at an appropriate retracted position from the tip of aspirator needle 52. Hence, when operation other than aspiratoration by aspirator needle 52 is carried out, the first embodiment asures operational safety that aspirator needle 52 is prevented from any displacement to protrude the tip of aspirator needle to a substantial depth of ovarian follicle 100b to injure the ovum or deeper tissue. The ovum can be aspirated and picked up efficiently within a short period fo time only by releaving the fixation and protruding the tip of aspirator needle 52 slightly forwards. In addition, if there is possibility of displacment of aspirator needle 52 when only the aspirator is operated for aspirating and picking up operations, aspirator needle 52 can be fixed at a postion in an appropriate depth in the ovarian follicle with ease. In addition, when aspirator needle is fixed, the operator can detach his hand from the fixed aspirator needle 52 and can perform other operation so that a single operator or a small number of operators can pick up the ovum.

It should be noted that the first embodiment is designed to aspirate and pick up the ovum by inserting aspirator needle 52 through picking-up needle 51, but means for aspirating and picking up the ovum are not retricted to such a structure but can be designed so that the means are incorporated with no aspirator needle 52 and provided no side hole 58 and aspirate and pick up the ovum directly from small hole 60. In such a case, it is preferred to infuse saline water, or the like, into the ovarian follicle 100b and aspirate and pick up the ovum together with the fused saline water. In such a modification eliminating aspirator needle 52, the trailing end of fine hollow member 55 is not fixed by handle member 56 but extended backwards to the portion for inserting aspirator needle 52 and fix the needle by means of holding and fixing means 70. In such a case, the inner diameter of inserting hole 83 should be, of course, compatible with the outer diameter of fine hollow member 55.

In picking-up needle 51, according to said first embodiment, the structure is not restricted to those biasing fine hollow member 55 to protrude it forwards by the action of spring 57, but is designed so that fine hollow member 55 is protruded or retracted manually. Sheath tube 53 may be protruded or retracted from fine hollow member 55.

In addition, the obliquely cut tip of sheath tube 53 may be modified so that the furthermost portion of tip is sharpened and the trailing portion of tip is rounded so as to pierce the furthermost portion and to form an opening by rotating the furthermost tip. In such a modification, the length of the furthermost sharpened portion of the tip is adjusted to about the thickness of ovarian follicle, the sharpened edge cannot pierce into the ovarian follicle so that the possibility for injuring the ovum can be eliminated substantially completely. Moreover, in such a case, the sharpened edge is limited to a lenght smaller slightly than the thickness of ovarian follicle to cut circularly the follicle to about the rounded portion 59 of fine hollow member 55, or the like, and to press the circular portion to provide an opening so as to be inserted into the follicle.

Still further, means for fixing aspirator needle 52 or fine hollow member 55, are not limited to those of the first embodiment but those fixing contact member 85 by pressing, for example, by a thread. Still further, if aspirator needle 52, or the like, can be fixed so as not to collapse aspirator needle 52, or the like, such means can be structured to be pressed directly. For example, if compression member 87 is made of soft material, such as rubber, or the like, aspirator needle 52, or the like, can be pressed and fixed directly.

Furthermore, when aspirator needle 52 is employed as means for aspirating and picking up the ovum, an aspirator such as syringe, or the like, may be incorporated without providing cock mouthpiece 98 at handle member 97. When aspirator needle 52 is not employed, the handle side of fine hollow member can be modified as mentioned above.

FIGS. 14 to 18 illustrates a second embodiment of this invention.

Abdominal endoscope according to the seond embodiment is same as shown in FIG. 1.

Figure 14:
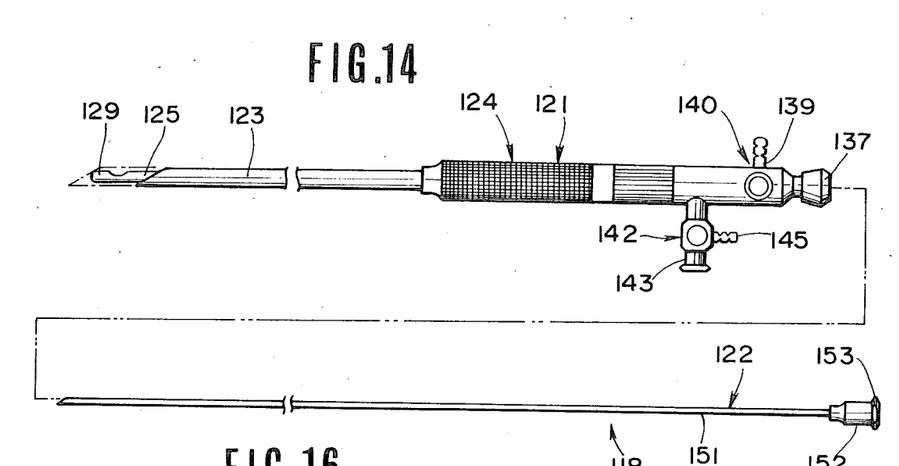
FIG. 14 shows a aspirator needle for picking up ovum according to the second embodiment.
Figure 15:
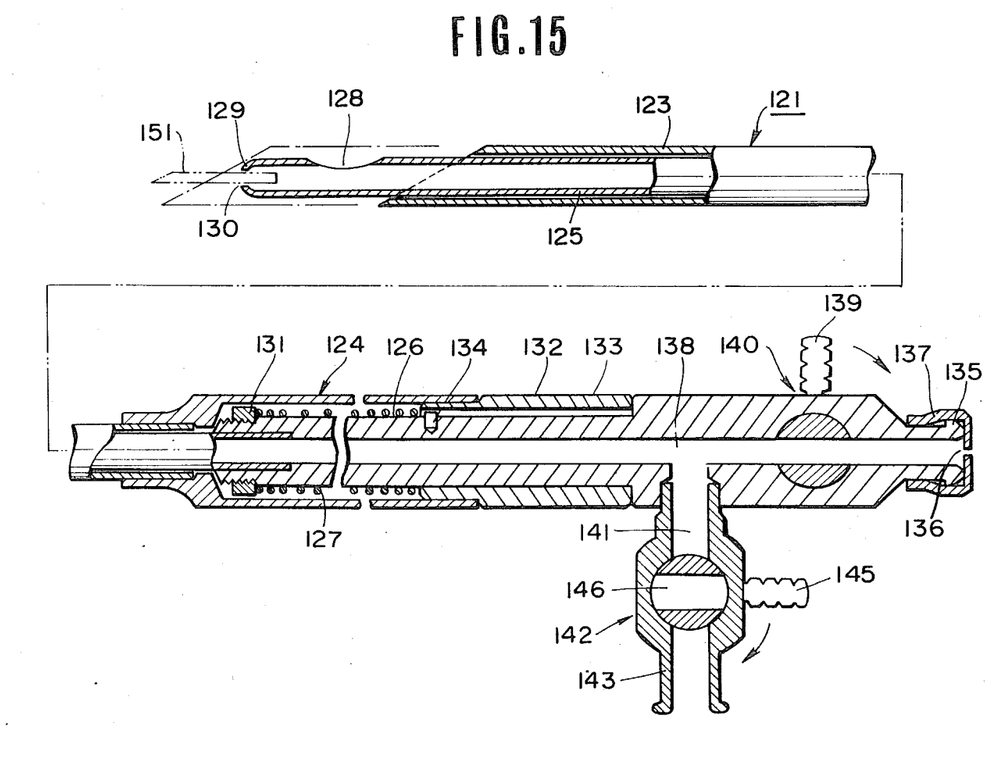
FIG. 15 shows an enlarged view of the aspirator tool of FIG. 14.

Tool 118 is picking up the ovum is insertable through channel 13 from the trailing end of channel memer 4 of the abdominal endsceope 1 and composed of picking-up needle 121, as shown separately in FIG. 14 or in FIG. 15 in enlarged scale, and hollow aspirator needle 122 insertable through the hollow passage within the picking-up needle 121.

Picking-up needle 121 is composes of elongated sheath tube 123 inserted through forceps channel 13 of abdominal endoscope 1, handle member 124 comprising tubular or cylindrical member having a larger diameter and connected with the trailing end of the sheath tube 123 and having the outer periphery thereof formed with knurled pattern for grasping it easily and fine hollow member 125 attached slidably axially or longitudinally within the sheath tube 123.

Figures 16, 17:
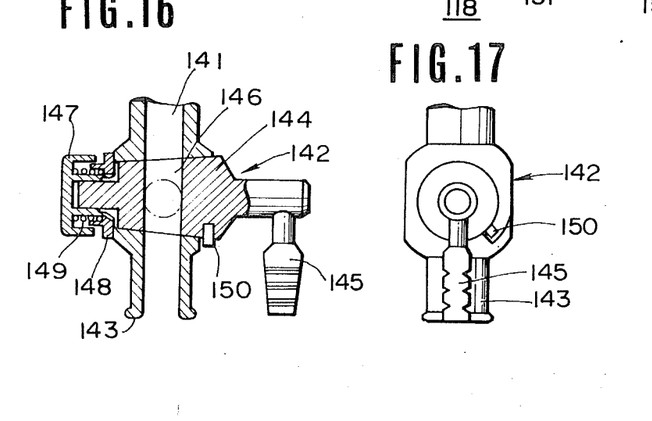
FIG. 16 shows an aspirator needle inserted from the trailing end of said aspirator tool.
FIGS. 17 and 18 illustrate the structure of the cock for the aspirator tool.

As shown in FIG. 15, the fine hollow member 125 within sheath tube 123 is secured fixedly to the inner periphery of thick-walled and substantially tubular main handle body 126 having the trailing end made of flexible elastic member at the leading end. The fine hollow member is biased by the action of spring 127 fitted around the clearance defined between the forward peripheral surface of main handl body 126 and the inner periphery of tubular member forming handle member 124 together with main handle body 126 so as to be protruded axially forwards. Namely, as shown in FIG. 16 or 17, the tip of fine hollow member 125 is cut obliquely so as to be protruded from the tip of sheath tube 123 comprising a sharp edge to an appropriate length. The tip side of the fine hollow member 125 is provided a hole at the side thereof, i.e. side hole 128 so as to infuse gas or physiological sodium chloride solution (referred hereinafter as saline water). The forward portion of side hole 128 is formed into spherically rounded converged tip 129. There is provided hole 130 at the furthermost portion of the converged tip so that aspirator needle 122 inserted through the central axis of fine hollow member 125 is protruded through hole 130.

Spring 127 acts to bias fine hollow member 125 to be protruded therefrom and the leading end is controlled by abutting, for example, against nut 131 threaded at the leading end of main handle body 126 and the trailing end thereof is controlled by abutting against the leading end of elastic tubular sliding member 132 connected with the trailing end of tubular member comprising handle member 124 and fitted around the outer periphery of main handle body 126 at about the central portion. Sliding member 132 is axially elongated groove 133 on the inner periphery fitted with main handle member 126. Guide pin 134 is received within elongated groove 133 and secured to main handle member 126 so that when the tip of fine hollow member 125 is retracted backwards by pressing it, main handle member 126 is retracted longitudinally and guide pin 134 is also displaced backwards within elongated groove 133. When guide pin 134 is abutted against the furthermost end of elongated groove 133, tip portion 129 of fine hollow tube 125 is retracted to the inside of obliquely cut tip of sheath tube 123. Moreover, in FIG. 16 or 17, sheath tube 123 is not displaced from the position as shown by the solid line to that as shown by chain line, but when fine hollow pipe 125 is retracted backwards, fine hollow pipe 125 is retracted to the position shown by the chain line in the inside of sheath tube 123.

Furthermore, fine hollow member 125 is attached normally so that side hole 128 is protruded from the tip of sheath tube 123 forwards. In such a case, the position can be minutely adjusted, for example, by the position for fixing nut 131. The position can also be adjusted by providing protrudedly guide pin 134 or another pin to main handle body 126 at a forward position from the leading end of sliding member 132.

Spring 127 acts to bias fine hollow member 125 so as to about tip 129 of fine hollow member against the ovarian follicle and to retract tip 129 together the elastic member comprising main handle body 126 by the weak force by pressing it. In such a case, the sharpened tip of sheath tube 123 can be protruded by displacing tip portion 129 of fine hollow member 125 as that the sharpened tip pierces the membrane of ovarian follicles.

Figure 18:
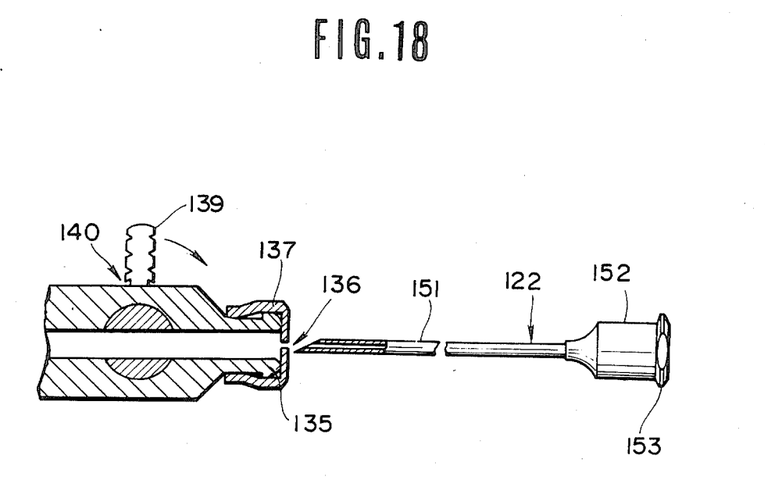

The training side of main handle body 126, which is vicinal to the portion attached with sliding member 132, is stepped to a larger diameter and the trailing end of stepped thick-walled portion is lathed to a small diameter to form cock mouthpiece 135 which is covered with rubber cap 137 provided with small hole 136 so as to insert aspirator needle 122 forwards through small hole 136 as shown in FIG. 18.

There is provided cock 140 at the thick-walled portion of main body 126 at a slightly forward position from cock mouthpiece 135 as so to close hollow passage 138 which is opened cock mouthpiece 135 when aspirator needle 122 is not inserted therethrough by the pivotal operation of lever 139.

There is also provided cock 142 which is provided through hole 141 for connecting hollow passage 138 of main handle body 126 so as to protruded, for example, downwards Cock 142 has, for example, structure as shown in FIGS. 17, 19 and 20.

Namely, through hole or passage 141 in cock 142 acts to connect cock mouthpiece 143 with hollow passage 138 of main handle body 126. Cock 142 has through hole having a higher diameter than that of through hole 141 rectangularly to the direction of through hole 141. Plug 144 is attached thereto. The through hole is tapered to one direction and ground plug 144 is fitted with the ground through hole so as to maintain the tightness. The trailing end, having a larger diameter of tapered plug, is lathed to a smaller diameter and provided rectangularly and protrudedly with lever 145. Plug 144 is pivoted by the rectangular pivotal operation of lever 145 so that through hole 146 formed through plug 144 is connected to through hole 141 as shown in FIG. 18 or blocked from the through hole as shown in FIG. 17 or by the chain line in FIG. 18. The opposite end of plug 144 is stepped to a smaller diameter and connected with nut 147. Nut 147 is provided with recess around the outer periphery contacted with the stepped portion of plug. Spring 149 is received within the space defined by the recess and confronted washer member 148 to press nut 147 to the direction opposite to plug 144 by the action of spring 149 so as to contact plug 144 closely with the ground through hole to maintain gas and liquid tightness.

Pin 150, provided protrudedly from plug 144, is a stopper for controlling the range of pivotal angle of lever 145.

Cock 140 has a similar structure.

Aspirator needle 122, which in insertable forward from rubber cap 137 of said picking-up needle 121, comprises fine hollow tube 151 inserted through hollow passage 138 of picking-up needle 121. Clamping member 152, having a larger diameter is connected with the trialing end of fine hollow tube 151. The trailing end of clamping member 152 is formed with a cock mouthpiece 153 for connection to an aspirator tool, such as syringe, or the like. The tip of hollow tube member 151 is cut obliquely, such as a needle of syringe, and the sharpended edge is designed to be protruded from small hole 130 provided at the rebounded tip after the sharpened tip of sheath tube 123 has been pierced into the membrane of ovarian follicle so that when the sharp edge of fine hollow tube 151 is pierced into the membrane of ovarian follicle, it picks up the ovum by the aspiration without injuring the ovum.

There will be now set forth how to pick up the ovum by means of the abdominal endoscope according to said second embodiment by way of FIG. 13.

When an alveoclar ovarian follicle is possibly grown on the surface of ovary, the abdominal wall of the mother's body is provided with a guide hole by piercing a trocar. Insert member 2 of abdominal endoscope 1 is inserted through the guide hole. A veress gas in infused through cock mouthpiece 22 provided at the vicinity of branch of second channel 5 for facilitating the insertion of laparoscope 1 for observation and subsequent picking up operatiion. Insert member 2 of abdominal endoscope 1 ins inserted and the ovary 100a connected to uterus 100 through fallopian tube 99 is observed by means of the optical system at the tip of insert member 2 as shown in FIG. 13. When the presence of alveoclar ovarian follicle 100b is confirmed on the surface of ovary 100a, the clamping forceps 25, which is inserted forwards from the trailing end of second channel 5 of abdominal endoscope 1 through passage 15, and picking-up needle 51, is inserted forwards through passage 14 within channel 4 from the trailing end of first channel 4.

The vicinity of grown ovarian follicle 100b is clampled by alligator mouth 46 at the tip of clamping forceps 25 protruded forwards through channel hole 13 of abdominal indoscope 1 by manipulating the handle side of forceps 25 under the observation of abdominal endoscope grasped by one hand and lock clamping forceps 25 under the clamped condition. Lever 40, of holding and fixing means 26, is pivoted. The pivotal operation of lever 40 permits compression member 37 to press flat member 35 of contact member 34, provided with split-ted groove 36, to reduce the effective inner diamerter and to hold and fix clamping forceps 25 inserted through channel hole 13 so as not be slidable axially. Accordingly, the operator can remove his hand from fixed clamping forceps 25 and effect the operation for protruding picking-up needle 121 forwards from the leading end of channel hole 13 to about the tip of needle 121 against ovarian follicle 100b to be operated and press it forwards gently and carefully. Then the protruded tip of fine hollow member 125 is retracted by the pressing of picking-up needle to protrude the tip having the sharp edge of sheath tube 123 and forms a small opening. When the opening is enlarged to a size capable to insert the converted tip of fine hollow member 125, the piercing of sharp tip of sheath tube 123 is stopped and tip 129 of fine hollow member 125 is protruded automatically to be inserted into ovarian follicle 100b through the opening. Because the vicinity of ovarian follicle 100b is clamped and fixed by means of alligator mouth 46 at the tip of clamping forceps 25, ovarian follicle 100b is prevented from displacement when the protruded tip of picking-up needle 121 can be pierced safely and correctly through the desired portion to form an opending for picking up the ovum. Moreover, rounded tip 129, of fine hollow member 125, has no possibility for injuring the ovum by inserting the tip into ovarian follicle 100b to a substantial depth. The ovum can be aspirated and picked up, together with the saline water or veress gas, from ovarian follicle 100b maintained under the normal condition or swollen by infusing the saline water or the like through side hole 128 of fine holow tube 125 from the rounded tip of aspirator needle 122 protruded through small hole 130 of fine hollow member 125. The ovum is picked up by connecting an aspirator, such as a syringe, with cock mouthpiece 153 at the trailing handling end of clamping means 152 for aspirator needle 122 by means of a tube and aspirating by the aspirator.

According to the second embodiment, because the abdominal endoscope is attached branchedly with two channels 4,5 capable to insert clamping forceps 25 in addition to picking-up needle 121, an opening for picking up the ovum can be formed safely and correctly under the condition that the vicinity of portion to be picked up by clamping forceps 25 and the ovum can be picked up conveniently by means of aspirator needle 122 inserted through small hole 130 of fine hollow member 125.

Furthermore, since holding and fixing means 26 is provided within channel 5 for inserting clamping forceps 25, the forceps can be fixed firmly. Accordingly, the picking-up operation can be done only by one operator, if desired. Moreover, holding and fixing means 26 do not fix the forceps locally by means of thread, etc., but pinch and fix the forceps over a wide area so that there is no fear to recess or deform the hollow member.

Still further, in the second embodiment, flexible clamping forceps 25 is inserted through bended second channel 5 and rigid picking-up needle 121 is inserted through straight first channel 4. However, such a mechanism is not limited so that a flexible picking-up needle may be inserted through the bended channel and the rigid clamping forceps through the straight channel which is provided, in turn, holding and fixing means.

The means according to this invention can be employed for picking up not only the human ovum, but also animal ovum such as milk cow, beef cattle, etc. which have commerically desired high-blooded strains.

It should be obvious that various embodiments over a wide range can be devised without departing from the spirit and scope of this invention. Hence, the present invention should not be limited to any embodiments except the subject matter as claimed in the attached claims.

What is claimed is:

1. Endoscope means having an elongated insert member which is insertable at one of its ends through a body cavity and having an observation optical system and an illuminating optical system and channels extending therethrough for receiving an operational tool from the outside of the body through said elongated member and into the body cavity in the axial direction of said elongated insert member, an inserting mouths branch at the handle side of one of said channels having a plurality of passages connecting to said one of said channels characterized by that at least one of said plurality of passages is provided with means for clamping and firmly fixing an operational tool inserted therethrough so as to prevent slidable axial movement of said operational tool in said at least one of said plurality of passages.

2. Endoscope means according to claim 1 further including air and liquid sealing means for sealing said tool in said at least one of said plurality of passages against air and liquid leakage.

3. Endoscope means according to claim 1 characterized by that said elongated insert has a main body member at the end of said insert member trailing said insertable end and is connected with a first inserting mouth in alignment with said inserting member, a second inserting mouth branched obliquely from said insert member backwards and an endoscopic eyepiece attached obliquely backwards to said insert member.

* * * * *